(12) United States Patent
Formosa et al.

(10) Patent No.: US 11,596,789 B2
(45) Date of Patent: *Mar. 7, 2023

(54) ADAPTOR

(71) Applicant: Medtronic, Inc., Minneapolis, MN (US)

(72) Inventors: Elizabeth K. Formosa, Robbinsdale, MN (US); Robert T. Sandgren, Lindstrom, MN (US); Kathryn E. Aman, St. Anthony, MN (US); Steven Deininger, Plymouth, MN (US); Paul Eichstaedt, Blaine, MN (US); Randy S. Roles, Elk River, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/948,857

(22) Filed: Oct. 2, 2020

(65) Prior Publication Data
US 2021/0101005 A1 Apr. 8, 2021

Related U.S. Application Data

(60) Provisional application No. 62/950,665, filed on Dec. 19, 2019, provisional application No. 62/950,663, filed on Dec. 19, 2019, provisional application No. 62/915,887, filed on Oct. 16, 2019, provisional application No. 62/910,566, filed on Oct. 4, 2019.

(51) Int. Cl.
*A61N 1/36* (2006.01)
*A61N 1/375* (2006.01)
*A61N 1/05* (2006.01)

(52) U.S. Cl.
CPC ....... *A61N 1/36007* (2013.01); *A61N 1/0551* (2013.01); *A61N 1/3606* (2013.01); *A61N 1/36125* (2013.01); *A61N 1/3752* (2013.01)

(58) Field of Classification Search
CPC .......................... A61N 1/36007; A61N 1/0551
USPC .......................................................... 607/41
See application file for complete search history.

(56) References Cited

U.S. PATENT DOCUMENTS

| 4,583,543 A | 4/1986 | Peers-Trevarton |
| 4,898,173 A | 2/1990 | Daglow et al. |
| 4,934,366 A | 6/1990 | Truex et al. |
| 5,000,177 A | 3/1991 | Hoffmann et al. |
| 5,413,595 A | 5/1995 | Stutz, Jr. |

(Continued)

OTHER PUBLICATIONS

Application and file history for U.S. Appl. No. 17/249,555, filed Mar. 4, 2021, inventors Sell et al.

(Continued)

*Primary Examiner* — Nadia A Mahmood
(74) *Attorney, Agent, or Firm* — Patterson Thuente IP

(57) ABSTRACT

An apparatus and method of electrically coupling a previously implanted stimulation lead with a replacement neurostimulator device. The apparatus and method configured to operably couple a proximal portion of a neuromodulation adaptor including a plurality of electrical conductors spaced apart at a first pitch spacing to a corresponding plurality of electrical terminals of a replacement neurostimulator device, and operably couple a distal end of the neuromodulation adaptor including a plurality of conductor elements and an electrically active set screw spaced part of a second pitch spacing to a corresponding plurality of electrical connectors of a previously implanted stimulation lead.

15 Claims, 19 Drawing Sheets

(56) References Cited

U.S. PATENT DOCUMENTS

| | | |
|---|---|---|
| 5,669,790 A | 9/1997 | Carson et al. |
| 5,843,141 A | 12/1998 | Bischoff et al. |
| 6,205,358 B1 | 3/2001 | Haeg et al. |
| 7,083,474 B1 | 8/2006 | Fleck et al. |
| 7,526,339 B2 | 4/2009 | Lahti et al. |
| 7,590,451 B2 | 9/2009 | Tronnes et al. |
| 7,736,192 B2 | 6/2010 | Alexander et al. |
| 7,860,568 B2 | 12/2010 | Deininger et al. |
| 7,881,783 B2 | 2/2011 | Bonde et al. |
| 8,123,567 B2 | 2/2012 | Kast et al. |
| 8,140,163 B1 | 3/2012 | Daglow et al. |
| 8,180,461 B2 | 5/2012 | Mamo et al. |
| 8,251,731 B2 | 8/2012 | Boyd et al. |
| 8,401,649 B2 | 3/2013 | Tronnes et al. |
| 8,525,027 B2 | 9/2013 | Lindner et al. |
| 8,831,744 B2 | 9/2014 | Swanson |
| 9,227,052 B2 | 1/2016 | Robnett |
| 9,427,574 B2 | 8/2016 | Lee et al. |
| 9,472,916 B2 | 10/2016 | Hanson et al. |
| 9,802,038 B2 | 10/2017 | Lee et al. |
| 9,855,423 B2 | 1/2018 | Jiang et al. |
| 10,905,871 B2 | 2/2021 | Nageri et al. |
| 2003/0073348 A1 | 4/2003 | Ries et al. |
| 2003/0163171 A1 | 8/2003 | Kast et al. |
| 2004/0176831 A1 | 9/2004 | Gliner et al. |
| 2008/0183236 A1 | 7/2008 | Gerber |
| 2012/0130438 A1 | 5/2012 | Seeley et al. |
| 2012/0203292 A1 | 8/2012 | Deininger et al. |
| 2014/0121741 A1 | 5/2014 | Bennett et al. |
| 2018/0078760 A1 | 3/2018 | Lee et al. |
| 2018/0175566 A1 | 6/2018 | Hanson et al. |
| 2019/0190215 A1 | 6/2019 | Hanson et al. |
| 2019/0336752 A1 | 11/2019 | Bauer et al. |
| 2019/0374776 A1 | 12/2019 | Mishra et al. |
| 2020/0398057 A1 | 12/2020 | Esteller et al. |

OTHER PUBLICATIONS

"Precision™ M8 Adapter Directions for Use", Boston Scientific Corporation, Jul. 2015.

"Precision™ S8 Adapter Directions for Use", Boston Scientific Corporation, Jun. 2018.

Matzel et al., "Sacral Neuromodulation: Standardized Electrode Placement Technique", Neuromodulation: Technology at the Neural Interface, vol. 20, Issue 8, Jun. 12, 2017, pp. 816-824.

Spinelli et al., "Evolution of a minimally-invasive procedure for sacral neuromodulation", Chapter 18: Development of Minimally-Invasive SNS, New Perspectives in Sacral Nerve Stimulation, Martin Dunitz Ltd., Mar. 28, 2002, pp. 217-222.

Axonics Modulation Technologies, "Axonics Prepares for Introduction of its Sacral Neuromodulation System", as featured in Business in Focus, Mar. 2018, a Focus Media Group Publication.

Blok et al., "Programming settings and recharge interval in a prospective study of a rechargeable sacral neuromodulation system for the treatment of overactive bladder", Neurourology and Urodynamics, vol. 37, Issue 52, Oct. 20, 2017, pp. 1-6.

Cohn et al., "Evaluation of the axonics modulation technologies sacral neuromodulation system for the treatment of urinary and fecal dysfunction", Expert Review of Medical Devices, vol. 14, No. 1, Dec. 4, 2016, pp. 3-14.

Elterman, "The novel Axonics® rechargeable sacral neuromodulation system: Procedural and technical impressions from an initial North American experience", Neurourology and Urodynamics, vol. 37, Issue S2, Dec. 19, 2017, pp. 1-8.

U.S. Appl. No. 16/948,859, filed Oct. 2, 2020, Inventor(s): Deininger et al.

U.S. Appl. No. 16/948,856, filed Oct. 2, 2020, Inventor(s): Sandgren et al.

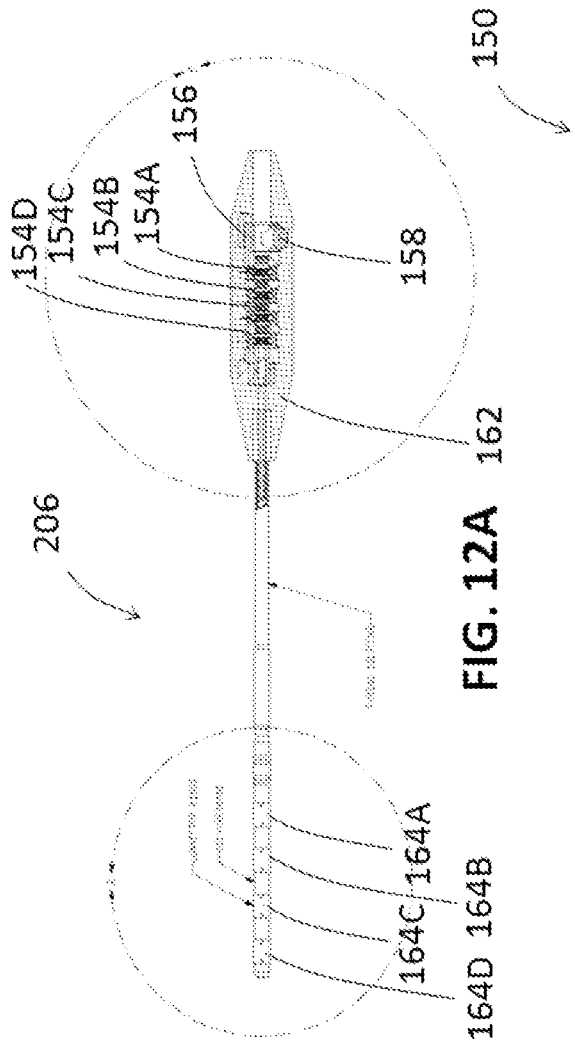
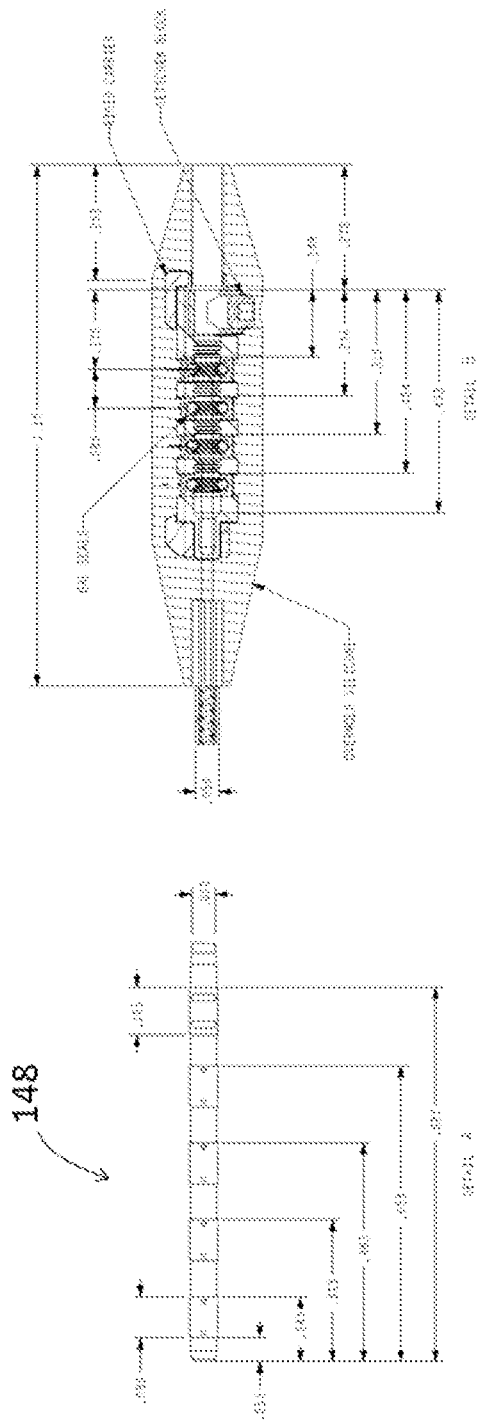
FIG. 12A
FIG. 12B
FIG. 12C

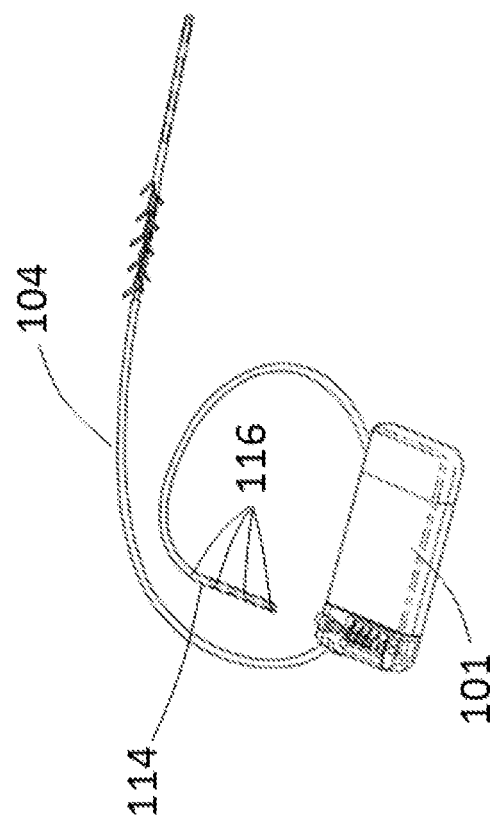

ADAPTOR

CROSS-REFERENCE TO RELATED APPLICATIONS

The present application claims the benefit of U.S. Provisional Application No. 62/950,663, filed Dec. 19, 2019, U.S. Provisional Application No. 62/950,665, filed Dec. 19, 2019, U.S. Provisional Application No. 62/915,887, filed Oct. 16, 2019, and U.S. Provisional Application No. 62/910,566, filed Oct. 4, 2019, the disclosures of which are hereby incorporated by reference in their entireties.

FIELD

The present technology is generally related to methods, systems and devices related to electrical stimulation therapy.

BACKGROUND

A number of human bodily functions are affected by the nervous system. For example, bodily disorders, such as urinary incontinence, urinary urge/frequency, urinary retention, pelvic pain, bowel dysfunction (constipation, diarrhea, etc.), erectile dysfunction, etc. are all bodily functions influenced by the sacral nerves. One technique to treat such bodily disorders is sacral nerve stimulation therapy. Sacral nerve stimulation therapy is a treatment that uses a small device to send mild electrical impulses to nerves located in the lower region of the spine (just above the tailbone). These nerves, referred to as sacral nerves (specifically S2, S3 and S4), influence the behavior of structures such as the bladder, sphincter and pelvic floor muscles. In some cases, electrical stimulation of the sacral nerves can successfully eliminate or reduce the above mentioned bodily disorders.

Generally, implantation of a sacral neuromodulation system involves surgically implanting a stimulation lead near the sacral nerves. The stimulation lead is a small, insulated, electrical conductor with stimulation electrodes on the distal end for implementation near the sacral nerves, and an electrical connector on the proximal end of the lead. The proximal end electrical connector is typically connected to an implantable neurostimulator device that operates in a fashion broadly similar to that of a cardiac pacemaker by delivering occasional mild electrical pulses to the sacral nerve of the patient.

The power used to generate the mild electrical pulses typically originates from a primary cell or battery located in the implantable neurostimulator device. Over an extended period of use, the battery can become depleted. For example, some currently available implantable neurostimulator devices may have a battery lifetime about ten years or less. Once the battery is depleted, it is common for patients to have the neurostimulator device replaced.

The emergence of implantable neurostimulator devices with rechargeable batteries has reduced the form factor of such devices. A rechargeable battery may be configured to last only a period of weeks between charges, and thus may be physically smaller in size than a battery intended to last years. As a result of this reduced size, the design of the stimulation leads compatible with newer devices has also changed. In particular, the size or configuration of the electrical connector on the proximal end of the lead has been reduced in size for improved mating with the smaller neurostimulator devices. As a result, some legacy and current stimulation leads may not be compatible with emerging and/or next-generation neuromodulation devices.

By contrast to the neurostimulator device, the stimulation leads typically have a much longer usable lifetime than the neurostimulator device. Further, replacement of the stimulation lead is typically considered a more invasive procedure, as unlike the neurostimulator device which is generally located just beneath the skin of the patient, the stimulation leads extend much further into the patient and are considered to be more challenging to place correctly. Additionally, many leads include one or more tines or barbs positioned on the distal end of the lead, which serve to anchor the lead in place within the patient as tissue fills in around the lead over time. Accordingly, it is generally considered preferable to leave the stimulation lead in place when the neurostimulator device is replaced. Unfortunately, not all stimulation leads are compatible with all neurostimulator devices. The present disclosure addresses this concern.

SUMMARY

The techniques of this disclosure generally relate to a neuromodulation adaptor configured to enable an electrically compatible connection between otherwise incompatible leads and neurostimulation devices, for example between a previously implanted stimulation lead and a replacement neurostimulator device, so as to increase physician or patient options in replacing components of a neuromodulation system. A number of factors may cause incompatibility between an implantable stimulation lead and a neurostimulator device, such as variation in the number of electrodes (e.g., one, two, four, etc.) included on the lead, the spacing of electrical contacts on the lead in the region where the lead is connected to the neurostimulator device, diameter of the lead, and use of active or inactive set screws, for example.

The present disclosure provides neuromodulation adaptor embodiments, including a proximal portion and a distal portion. The proximal portion can include a plurality of electrical conductors spaced apart at a first pitch spacing and configured to electrically engage with the corresponding plurality of electrical terminals of a neurostimulator device. The distal portion can include a plurality of conductor elements and a set screw, the plurality of conductor elements and set screw can be spaced apart at a second pitch spacing and can be configured to electrically engage with a corresponding plurality of electrical connectors of a stimulation lead. The first pitch spacing can have a pitch spacing of at least one of about 0.170 inches, about 0.085 inches or about 2 millimeters (about 0.080 inches), while the second pitch spacing can have a pitch spacing of about 0.170 inches, about 0.085 inches or about 2 millimeters (about 0.080 inches), wherein the first pitch spacing is different from the second pitch spacing, thereby enabling an electrical coupling between an otherwise incompatible stimulation lead and a replacement neurostimulator device.

In some embodiments, the proximal portion of the neuromodulation adaptor can include a forward stop configured to serve as a reference point for spacing of the plurality of electrical conductors relative to a corresponding plurality of electrical terminals of a neurostimulator device. In some embodiments, the distal portion can include a datum reference configured to serve as a reference point for spacing of the plurality of conductor elements relative to a corresponding plurality of electrical connectors of a stimulation lead. In some embodiments, the neuromodulation adaptor can further include a flexible portion located between the proximal portion and the distal portion, configured to enable bending of the neuromodulation adaptor to aid in an ideal positioning of a neurostimulator device relative to a stimulation lead within a body of a patient. In some embodiments, the neuromodulation adaptor can further include a septum configured to provide a fluid resistant seal to inhibit contact between an electrically active set screw and a bodily fluid.

The details of one or more aspects of the disclosure are set forth in the accompanying drawings and the description below. Other features, objects, and advantages of the techniques described in this disclosure will be apparent from the description in the drawings, and from the claims.

BRIEF DESCRIPTION OF DRAWINGS

FIG. 12A is a cross-sectional, profile view depicting an adaptor, in accordance with a sixth embodiment of the disclosure.

FIG. 12B is a close-up, partial cross-sectional view depicting a proximal portion of the adaptor of FIG. 12A.

FIG. 12C is a close-up, partial cross-sectional view depicting a distal portion of the adaptor of FIG. 12A.

FIG. 16A is an assembly view depicting a previously implanted neurostimulator device and stimulation lead, in accordance with the prior art.

Figure 1:
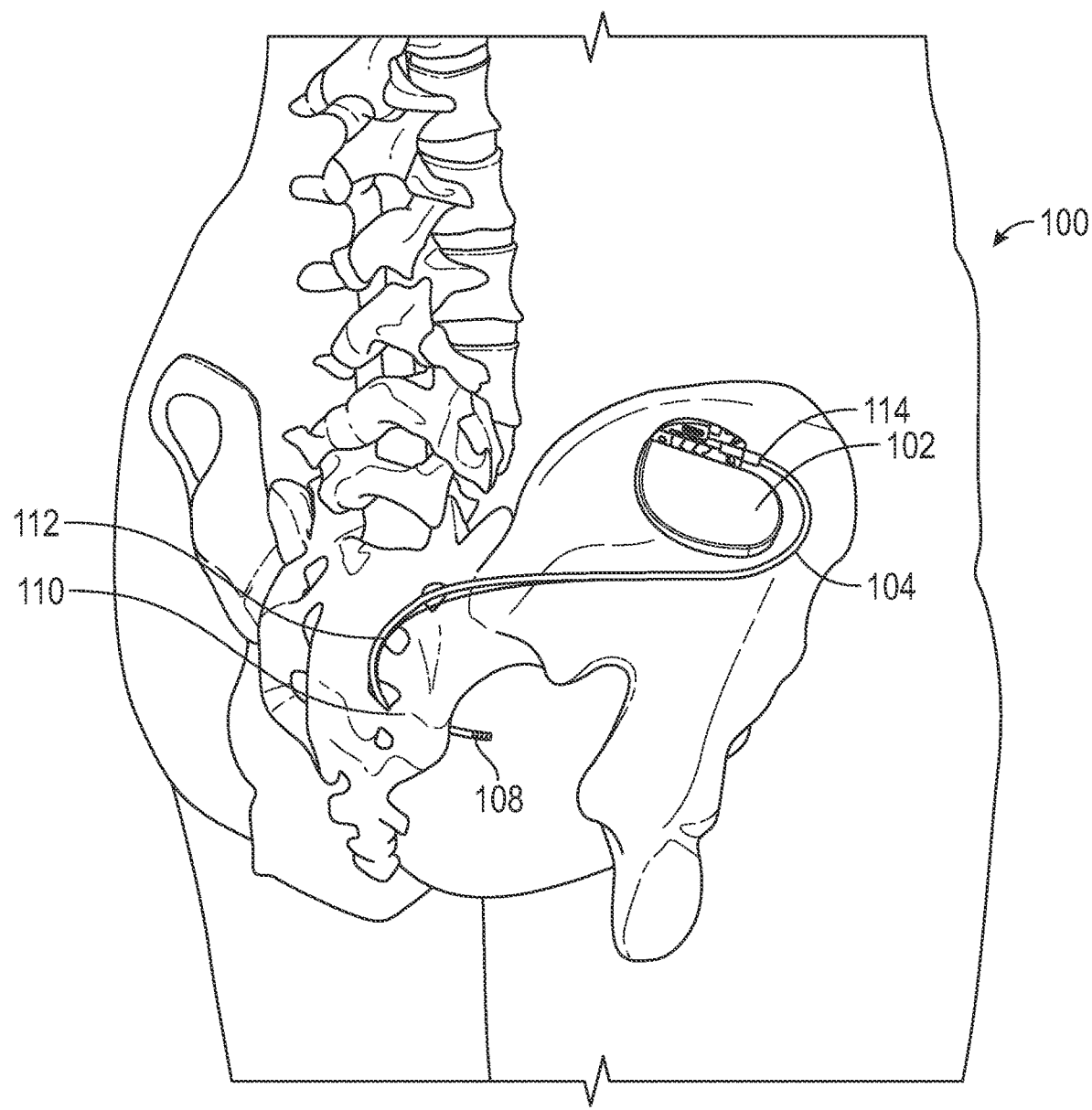
FIG. 1 is a schematic view depicting an implanted neuromodulation system adapted for sacral nerve stimulation, in accordance with the prior art.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

FIG. 1 schematically illustrates an example of an implemented neuromodulation system 100 adapted for sacral nerve stimulation. Neuromodulation system 100 includes a neurostimulator device 102 implanted in a lower buttock region of a patient, connected to an implanted stimulation lead 104 extending through a foramen for stimulation of a sacral nerve. As depicted in FIG. 1, the stimulation lead 104 is oriented through the S3 foramen, although other locations such as S2 or S4 are also contemplated. The stimulation lead 104 can include a distal portion 108 including one or more stimulation electrodes 110 configured to transmit electrical pulses to a nerve, nerve tissue, or other target site within a patient. In one embodiment, the stimulation electrodes 110 can be configured as an array of two, three, four or more ring-shaped electrodes for delivering electrical stimulation. In other embodiments, the stimulation lead 104 can include a greater or lesser number of electrodes. The proximal portion 114 of the stimulation lead 104 is plugged into the neurostimulator device 102, for example via a header of device 102.

The stimulation lead 104 is anchored by a tined anchor portion 112 that maintains a position of a set of stimulation electrodes 110 along or otherwise proximate a targeted nerve. Over time, tissue surrounding the stimulation lead 104 can grow between the tines 112, thereby aiding in securing the stimulation lead 104 in a fixed position relative to the nerve or other target site within a patient. The stimulation lead can have a variety of shapes, can be a variety of sizes, and can be made of a variety of materials, which size, shape, and materials can be tailored to the specific treatment application. The electrical pulses generated by the neuromodulation system 100 are delivered to one or more targeted sacral nerves via one or more stimulation electrode 110 at or near the distal portion 108 of the stimulation lead 104.

The pulsed electrical stimulation may be to one of several nerves; however for purposes of describing the system 100, the stimulation site is referred to herein simply as "sacral nerves." It should be understood that the term "sacral nerves" as used herein includes sacral nerves S1, S2, S3, S4, as well as other nerve sites such as pudendal nerve, superior gluteal nerve, lumbo-sacral trunk, inferior gluteal nerve, common fibular nerve, tibial nerve, posterior femoral cutaneous nerve, sciatic nerve, and obturator nerve. Additionally, stimulation may be provided unilaterally or bilaterally via two leads.

While this embodiment is adapted for sacral nerve stimulation, it is appreciated that similar systems can be used to provide therapy for urinary incontinence, urological disorders and or fecal incontinence. The urological disorders include overflow incontinence, stress incontinence, overactive bladder (OAB), idiopathic chronic urinary retention, interstitial cystitis, neural urological disorder, vescico-urethral dysfunctions, bladder inflammation, bladder pain, pelvic pain, genito-urinary disorders, such as prostatitis, prostatagia, and prostatodynia. Electrical stimulation is typically delivered to the sacral nerve root S3, but may be delivered to the S2, S4 or other sacral nerves or branches such as the pudendal nerves or perineal nerves. In other applications, the stimulation leads 104 may be, for example, implemented in a peripheral portion of a patient's body, such as in the arms or legs, and can be configured to deliver electrical pulses to the peripheral nerve, such as may be used to relieve chronic pain. Stimulation may be applied in bipolar mode, or in unipolar mode where the neurostimulator device 102 is used as an anode. It is appreciated that the stimulation leads 104 and/or the stimulation programs may vary according to the nerves being targeted.

Figure 2:
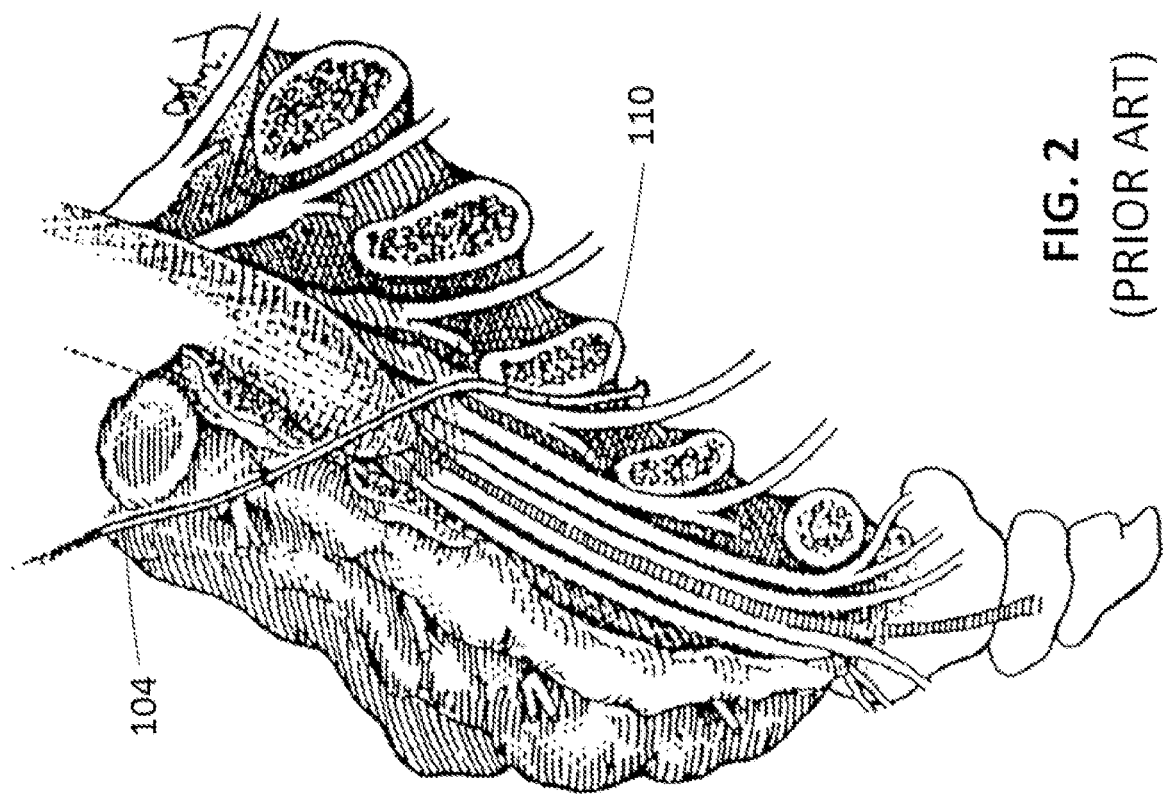
FIG. 2 is a schematic view depicting a stimulation lead implanted near a sacral nerve for stimulation, in accordance with the prior art.

FIG. 2 depicts an overall schematic of the sacral nerve area with the stimulation lead 104 implanted near a sacral nerve for stimulation. The stimulation lead 104 is inserted by first making an incision appropriate to the size of the patient and then splitting the paraspinal muscle fibers to expose the sacral foramen. A physician then locates the desired position and inserts the stimulation lead into the foramen and anchors the stimulation lead 104 in place. The stimulation lead 104 should be placed close enough to the nerve bundles such that the electrical stimulation results in a desired physiological response. The desired physiological response varies depending on which pelvic floor disorder is being treated or which nerve is being stimulated. The preferred position for the implantable lead 104 is implementation in close proximity to the nerve; as such placement results in the most efficient transfer of electrical energy.

To determine the best location of the stimulation lead 104, an insulated needle with both ends exposed for electrical stimulation is often used to locate the foramen and locate the proximity of the nerve by electrically stimulating the needle using an external pulse generator. The location is tested by evaluating the physiologic response and by the electrical threshold required to get that response. Once the appropriate location has been determined using the insulated needle, the stimulation lead 104 is implanted in that approximate location. In some embodiments, the stimulation lead 104 is advanced through the foramen until the electrodes 110 are positioned at the anterior sacral nerve root, while the anchoring portion 112 of the lead 104 proximal to the stimulation electrodes 110 are generally positioned dorsal of the sacral foramen through which the lead 104 passes, so as to anchor the lead 104 in position. A proximal portion 114 of the stimulation lead 104 is tunneled subcutaneously to a site where the neurostimulator device 102 is implanted, which is usually in the lower abdominal area (or may be in the gluteal region). The neurostimulator device 102 is connected to the proximal portion 114 of the stimulation lead 104, placed in a subcutaneous pocket, and the tissues are surgically closed in layers. Stimulation therapy can be applied after the tissues are healed from the surgery.

The neurostimulator device 102 may be explanted and replaced if needed, with relative ease. Reasons for replacing neurostimulator device 102 may include battery depletion, malfunctioning of the device, or desire to upgrade to a newer generation device. In contrast, replacement of a stimulation lead 104 after initial implant is typically undesirable. This is due, in part, because tissue surrounding the stimulation lead 104 typically grows between the tines 112 such that removal of the stimulation lead 104 may cause trauma to the surrounding tissue. Additionally, if a previously implanted stimulation lead 104 was properly positioned to deliver effective therapy to the patient, a surgeon is unlikely to replace the existing lead, avoiding the need to reevaluate positioning of a replacement lead for a proper physiological response with an insulated needle and external pulse generator, as described above. Accordingly, unless it is determined that the stimulation lead 104 is not functioning properly or is damaged, it is preferable to reuse a previously implanted stimulation lead 104 should the neurostimulator device 102 require replacement.

Figure 3:
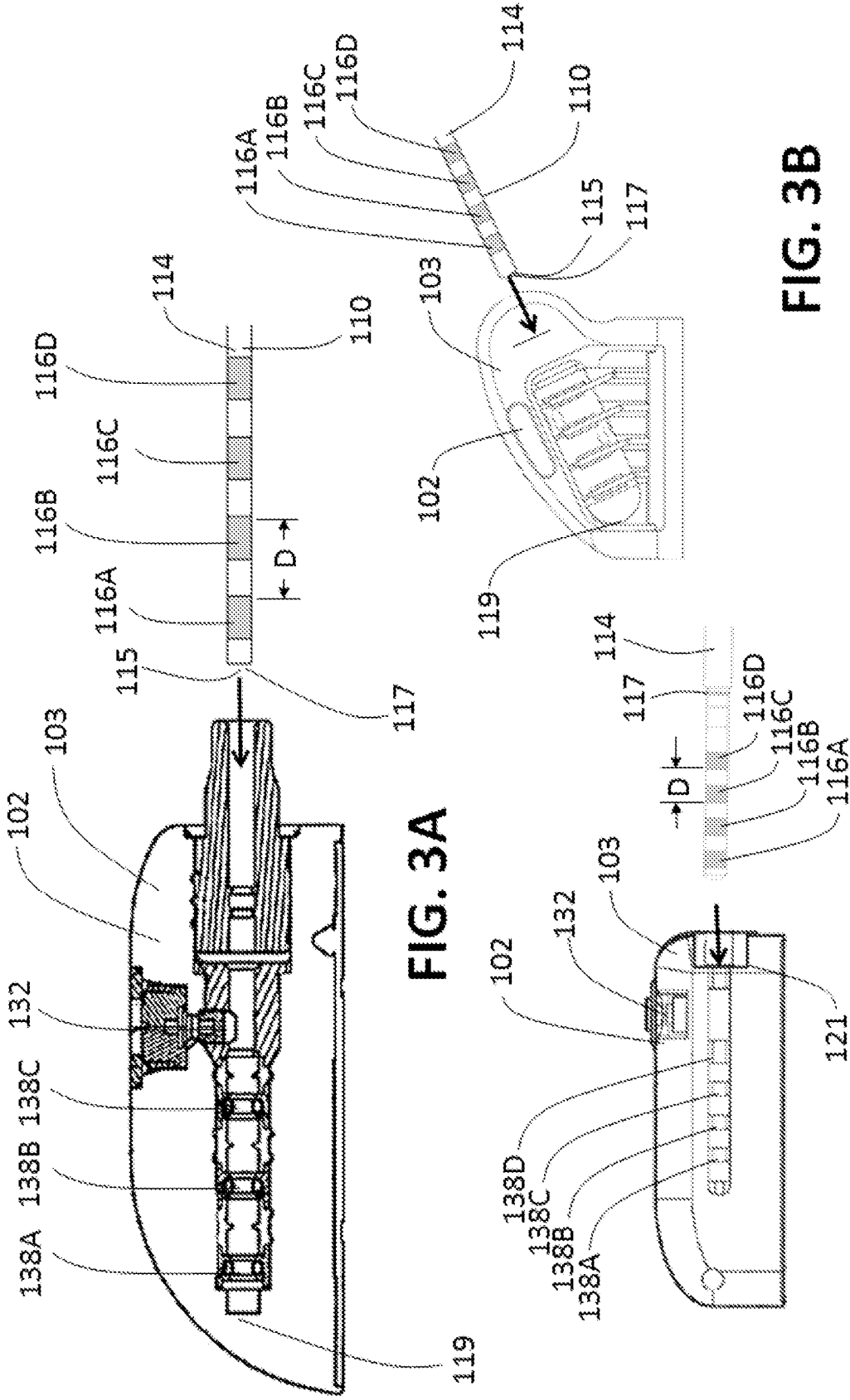
FIG. 3A is a cross-sectional profile view depicting a proximal portion of a stimulation lead and a neurostimulator device, in accordance with a first embodiment of the disclosure.
FIG. 3B is a cross-sectional profile view depicting a proximal portion of a stimulation lead and a neurostimulator device, in accordance with a second embodiment of the disclosure.
FIG. 3C is a cross-sectional profile view depicting a proximal portion of a stimulation lead and a neurostimulator device, in accordance with a third embodiment of the disclosure.

With additional reference to FIGS. 3A-C, the proximal portion 114 of the stimulation lead 104 can include one or more electrical connectors 116 configured to be operably coupled to a neurostimulator device 102 or adaptor 106 (alternatively referred to herein as an "adapter"). As depicted, the proximal portion 114 can include an array of four insulated ring-shaped connectors; although a greater or lesser number of connectors is also contemplated.

As depicted, the connectors 116 can be separated or spaced apart from one another at a fixed distance D, alternatively referred to as "pitch spacing" or "pitch." For example, in one embodiment, the plurality of connectors 116A-D can be spaced apart from one another at a pitch of approximately 0.170 inches (as depicted in FIG. 3A). In another embodiment, the plurality of connectors 116A-D can be spaced apart from one another at a pitch of approximately 0.085 inches (as depicted in FIG. 3B). In yet another embodiment, the plurality of connectors 116A-D can be spaced apart from one another at a pitch of approximately 2 mm (as depicted in FIG. 3C). Other pitch configurations are also contemplated. In addition to varying pitch configurations, stimulation leads 104 can differ in their outer diameter dimensions, general shape (e.g., blunt, tapered or rounded proximal end 115), as well as other physical characteristics.

In some embodiments, the proximal portion 114 can include a datum reference 117 configured to serve as a reference point for the spacing of the various connectors 116 or configured to serve as a physical stop when inserting the lead into a neurostimulator. For example, in one embodiment, the datum reference 117 can be located on the proximal end 115 of the stimulation electrode 110 (as depicted in FIGS. 3A and 3B), such that insertion of the lead 104 into the neurostimulator device until the datum reference 117 (e.g., proximal end 115) contacts a forward stop 119 thereby aligns the connections 116A-D of lead 104 with corresponding connector elements 138A-D of a header 103 of the neurostimulator device 102 and/or adapter 106. In another embodiment, the datum reference 117 can be located distally from the connectors 116A-D (as depicted in FIG. 3C), such that insertion of the lead 104 into the header 103 until the datum reference 117 contacts an abutting surface 121 thereby aligns the connectors 116A-D of lead 104 with corresponding connector elements 138A-D of the header 103 and/or adapter 106.

In some embodiments, the neurostimulator device 102 and/or adapter 106 can include a set screw 132 configured to tighten against the proximal portion 114, thereby enabling the proximal portion 114 of the stimulation lead 104 to be secured in position relative to the neurostimulator device 102 and/or adapter 106. In some embodiments, the set screw 132 can be configured to contact at least one of the connectors 116D (as depicted in FIG. 3A), so as to be electrically active. In other embodiments, (as depicted in FIG. 3C) the set screw 132 can be electrically inactive, in that it does not contact any of the connectors 116A-D, but may rather contact another portion of the stimulation lead, such as the datum reference 117.

Figure 4:
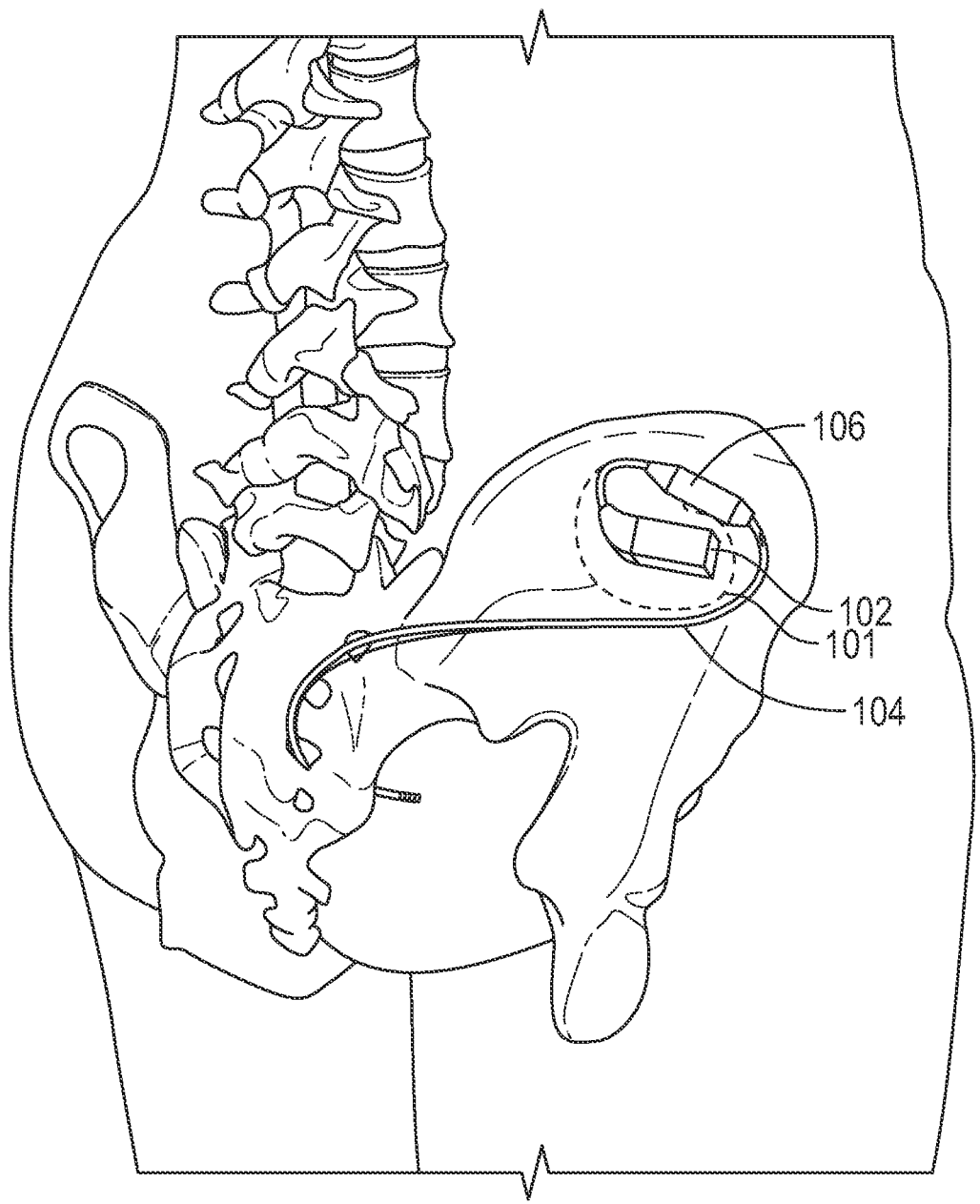
FIG. 4 is a schematic view depicting an implanted neuromodulation system adapted for sacral nerve stimulation, in accordance with the disclosure.
Figure 5B:
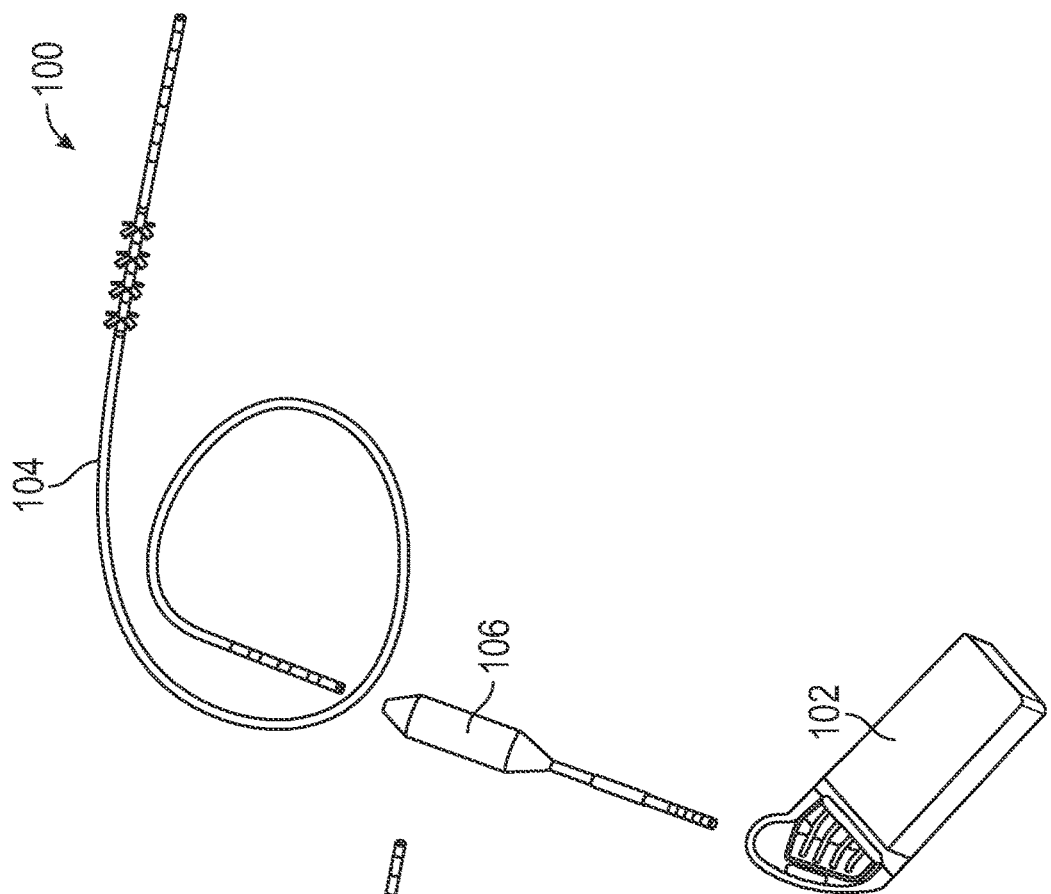
FIG. 5B is an assembly view depicting an adapted neuromodulation system, including a replacement neurostimulator device, previously implanted stimulation lead, and adaptor electrically coupling the otherwise incompatible stimulation lead and replacement neurostimulator device, in accordance with a first embodiment of the disclosure.
Figure 5A:
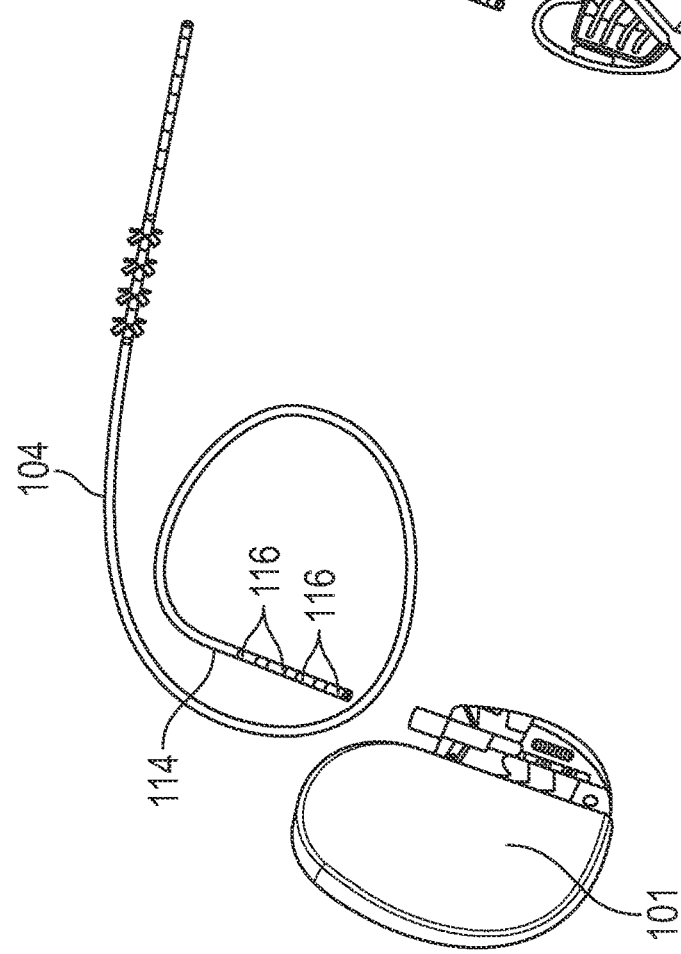
FIG. 5A is an assembly view depicting a previously implanted neurostimulator device and stimulation lead, in accordance with the prior art.

With reference to FIGS. 4 and 5A-B, in some cases it may be desirable to replace a previously implanted neurostimulator device 101 with a replacement device 102, particularly where the previously implanted device has reached or is nearing the end of its serviceable life (e.g., the previously implanted neurostimulator device may have a primary cell or battery that is near exhaustion), or is otherwise not functioning as desired. In such cases, the replacement device 102 may be more compact and/or have a different shape than the previously implanted device. For example, FIG. 4 depicts an outline of an Interstim II sacral neuromodulation neurostimulator device 101 (manufactured and sold by Medtronic), into which a replacement neurostimulator device 102 can be positioned. Accordingly, a replacement neurostimulator device 102 can differ both in shape and size from the previously implanted device 101. For example, the previously implanted device 101 can be a "large neuromodulation device," having a volume of at least 10 cubic centimeters (e.g. the Interstim II device, having a volume of about 14 cc), while the replacement neurostimulator device 102 can be a "small neuromodulation device," having a volume of about 10 cc or less or about 5 cc or less (e.g., the Axonics r-SNM from Axonics Modulation Technologies having a volume of about 5 cc, or the Medtronic Interstim Micro device, having a volume of about 3.5 cc). Alternatively, the previously implanted device 101 can be a small neuromodulation device, and the replacement neurostimulator device 102 can be a large neuromodulation device. The stated volumes of such devices generally refer to the implantable medical device only, and do not include any associated leads or adapters which may be coupled to such devices.

Other differences may include the orientation or angle at which the stimulation lead extend from the devices 101, 102, as well as the connector 116 pitch spacing of the stimulation leads designed to be used with the different devices 101, 102. For example, a previously implanted stimulation lead may have an electrical connector with a pitch spacing of about 0.170 inches, while the replacement neurostimulator device 102 may be configured to receive a stimulation lead having connectors 116 with a pitch spacing of about 0.085 inches or about 2 mm (about 0.080 inches). Accordingly, without modification, such as an adapter 106, a replacement device 102 may be incompatible with a previously implanted stimulation lead 104.

FIG. 5A depicts a previously implanted neurostimulator device 101 and stimulation lead 104, wherein the proximal portion 114 of the stimulation lead 104 includes connectors 116 having a pitch spacing of about 0.170 inches. FIG. 5B depicts a replacement neurostimulator device 102 configured to mate with a stimulation lead having a pitch spacing of about 0.085 inches. As further depicted in FIG. 5B, an adapter 106 can be used to connect the stimulation lead 104 to the replacement device 102, thereby providing an electrical coupling between an otherwise incompatible stimulation lead 104 and neurostimulator device 102.

Figure 6:
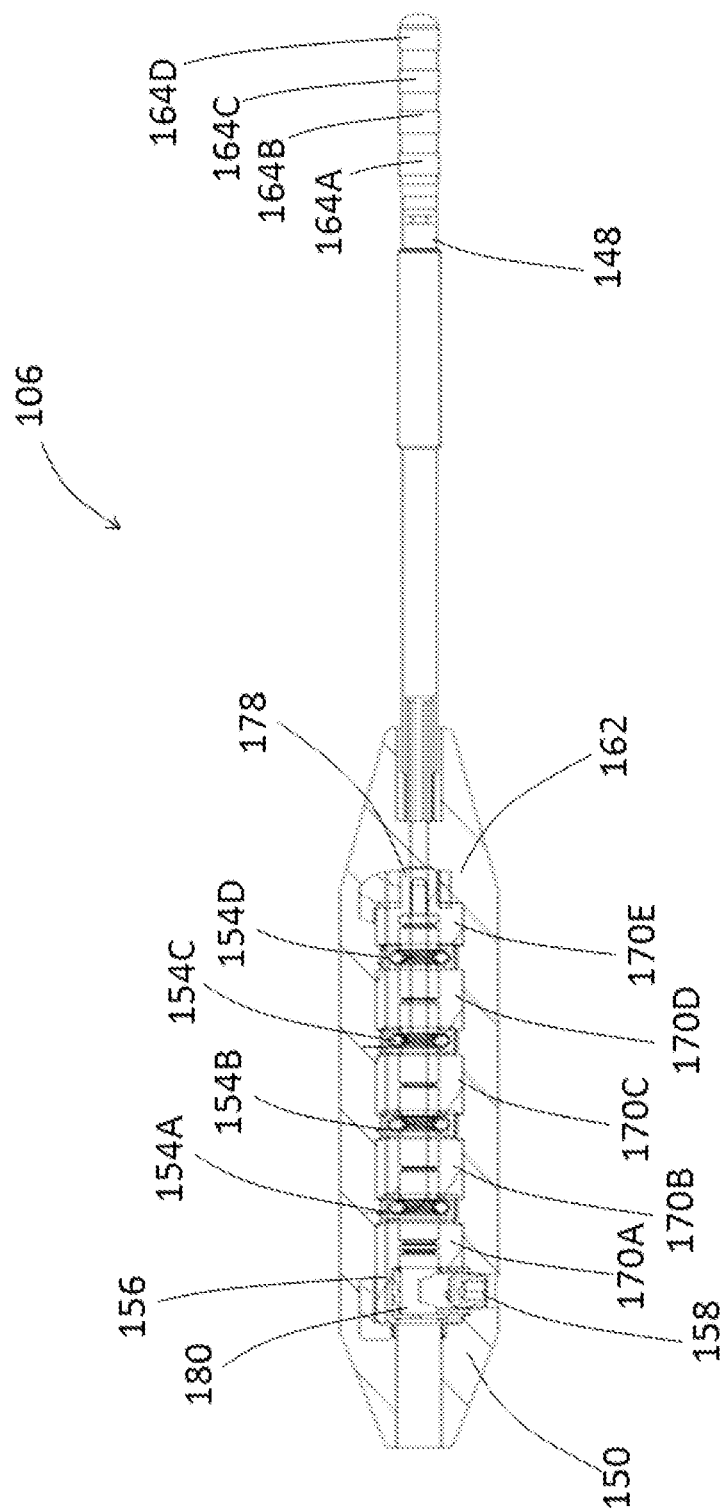
FIG. 6 is a cross-sectional, profile view depicting an adaptor, in accordance with a first embodiment of the disclosure.

With additional reference to FIG. 6, in one embodiment, the adapter 106 can include a proximal portion 148 configured to be received within a stimulation lead port of a neurostimulator device 102, and a distal portion 150 configured to receive a proximal portion of a stimulation lead 104. In one embodiment, the adapter 106 can include a plurality of connector elements 154A-D, a set screw block 156, a set screw 158, a boot 162, and a plurality of electrical conductors 164A-D.

In one embodiment, the connector elements 154A-C can form complete circular structures, examples of which include Bal Seal® canted coil connectors. The connector elements 154A-C can be separated from one another by insulative spacers 170A-E, such that the connector elements 154A-C and insulative spacers 170A-E are interleaved along a longitudinal axis of the distal portion 150. The insulative seals 170A-E can provide wiper seals, and can be constructed of a biocompatible compliant material such as silicone. In some embodiments, the insulative seals 170A-E can be compressible to some degree along the longitudinal axis, so as to create a tight fit between adjacent connector elements 154.

In one embodiment, the set screw block 156 can be configured to enable threaded insertion of the set screw 158 into the set screw block 156. In some embodiments, the set screw block 156 can be axially aligned with the connector elements 154A-C, such that the electrically active set screw 158 contacts an electrical connector of a stimulation lead 104 inserted into the distal portion 150 of the adapter 106. In other embodiments, the set screw 158 can be electrically inactive.

Although the adapter 106 is depicted as having four connector elements 154A-C and an electrically inactive set screw 158, and five insulative seals 170A-E, other quantities of connector elements 154 and insulative seals 170 are also contemplated. For example, in one embodiment, the adapter 106 can include three connector elements 154 and an active set screw block 156, or four connector elements 154. Where a set screw 158 is present, the set screw 158 can be configured to tighten against a portion of a stimulation lead 104 received within the distal portion 150 of the adapter 106, thereby enabling the stimulation lead 104 to be secured in position relative to the adapter 106. In some embodiments, the set screw block 156 and/or the rear seal 160 can define a forward stop 178 and/or abutting surface 180 configured to interact with a datum reference 117 of the stimulation lead 104, to ensure that the electrical connectors of the stimulation lead 104 are appropriately positioned with respect to the connector elements 154 and/or set screw 158.

During assembly, the set screw block 156, connector elements 154A-C, insulative spacers 170A-E, and proximal connector portion 148 can be aligned, and the boot 162 can be applied to an exterior of the aligned assembly. For example, in one embodiment, the boot 162 can be constructed of liquid silicone rubber, over-molded over the set screw block 156, connector elements 154A-C, insulative spacers 170A-E and a portion of the proximal connector portion 148 extending therefrom.

The plurality of electrical conductors 164A-D can be positioned on the proximal portion 148. For example, in one embodiment, the adapter 106 can include four electrical conductors 164A-D configured to electrically couple to the corresponding electrical terminals of a neurostimulator device 102. For example, in some embodiments, the proximal portion 148 of the adapter 106 can be configured to be received within a header portion of the neurostimulator device 102 (as depicted in FIG. 3B). The electrical conductors 164A-D can be in electrical communication with the connector elements 154A/C and/or set screw block 156 via one or more wires, cables or other connecting elements. In some embodiments, a portion of the boot 162 located between the electrical conductors 164 and the connector elements 154 can be flexible, so as to enable bending of the adapter 106 to aid in an ideal positioning of the neurostimulator device 102 relative to the stimulation lead 104 within the body of a patient.

Accordingly, in some embodiments, the adapter 106 can be configured to establish a compatible electrical connection between a neurostimulator device 102 (which may be a replacement for a previously implanted neurostimulator device) and an implantable stimulation lead 104 (which may have been previously implanted into the patient). For example, in one embodiment, the neuromodulation adapter 106 can be configured to electrically connect a previously implanted stimulation lead 104 having a plurality of electrical connectors 116 spaced apart from one another at a first pitch with a replacement neurostimulator device 102 generally configured to mate with a stimulation lead 104 having a plurality of electrical connectors 116 spaced apart from one another at a second pitch. In embodiments, the first pitch can be approximately 0.170 inches, and the second pitch can be approximately 0.085 inches. Further, in some embodiments, the adapter 106 can be magnetic resonance imaging (MRI) compatible.

Figure 7A:
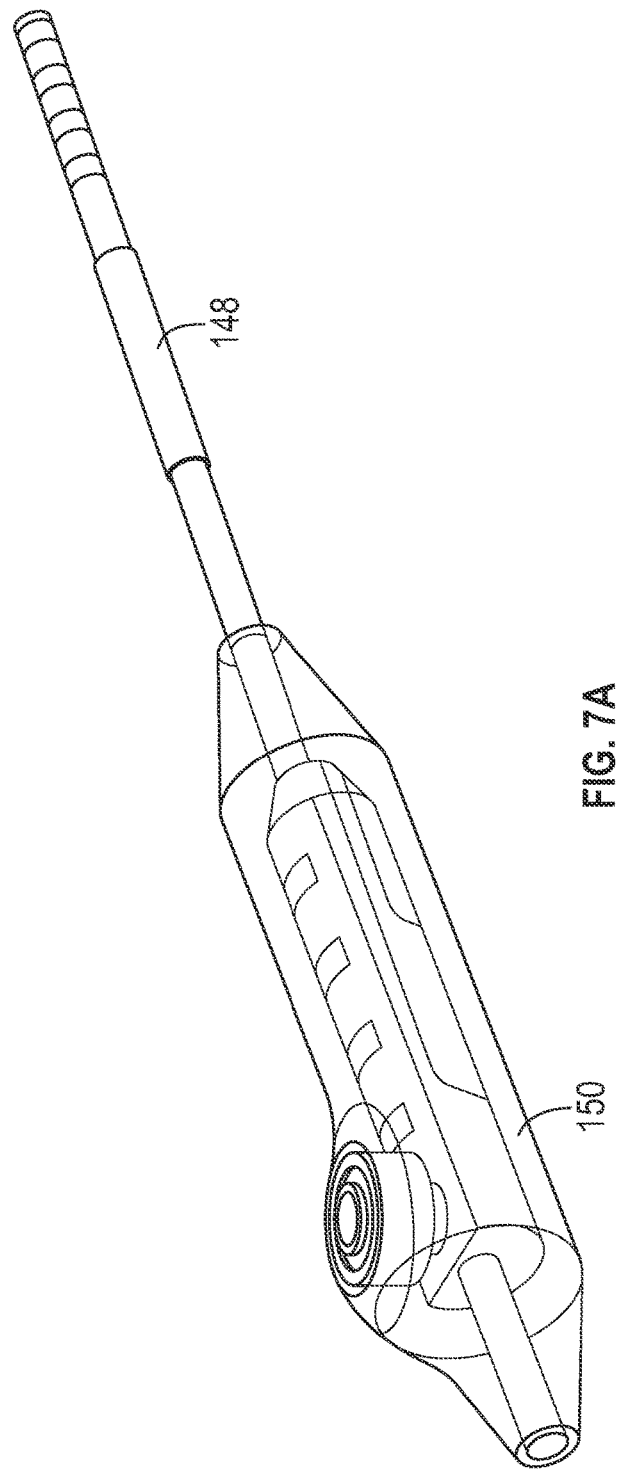
FIG. 7A is a perspective view depicting an adaptor, in accordance with a second embodiment of the disclosure.
Figure 7B:
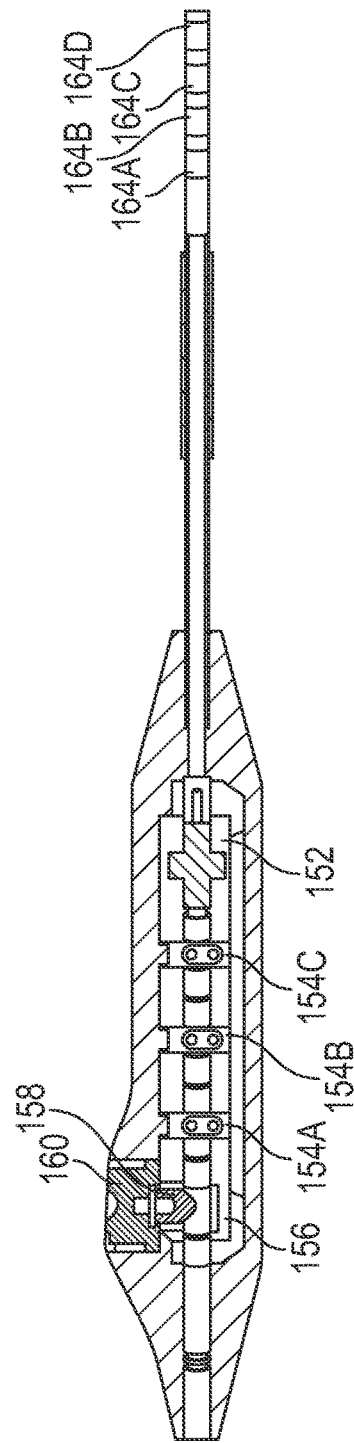
FIG. 7B is a cross-sectional, profile view depicting the adaptor of FIG. 7A.

FIG. 7A-B depict a second embodiment of a neuromodulation adapter 106' in accordance with the disclosure. In one embodiment, the adapter 106' can additionally include a chassis 152, into which the set screw block 156, connector elements 154A-C, insulative spacers 170A-C can be assembled, prior to overmolding of the boot 162. Additionally, in some embodiments, the adapter 106 can include a septum 160 configured to provide a fluid resistant seal to inhibit contact between the set screw 158 and bodily fluid.

In some embodiments, the boot 162 can extend outwardly, so as to form a mound or hump surrounding the septum 160.

Figure 8:
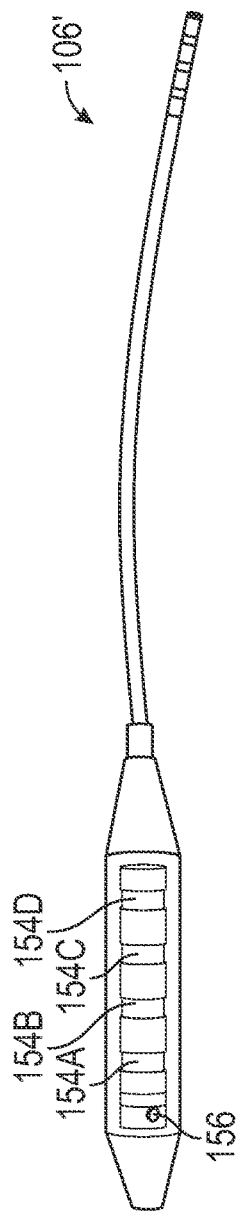
FIG. 8 is a profile view depicting an adaptor, in accordance with a third embodiment of a disclosure.
Figure 9:
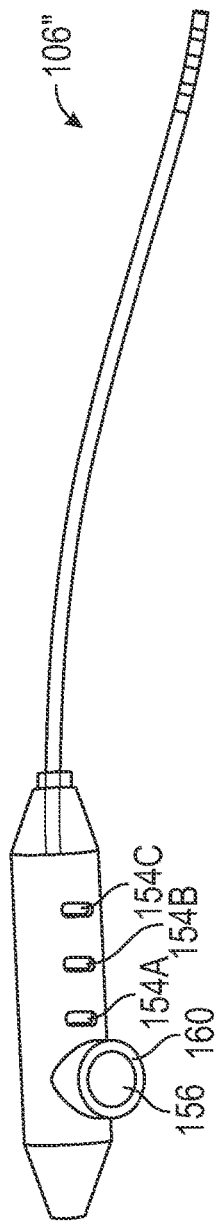
FIG. 9 is a profile view depicting an adaptor, in accordance with a fourth embodiment of a disclosure.
Figure 10:
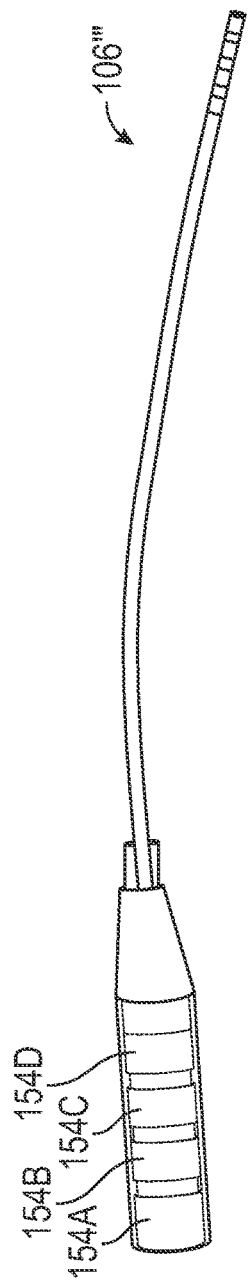
FIG. 10 is a profile view depicting an adaptor, in accordance with a fifth embodiment of a disclosure.

Other embodiments of neuromodulation adapter 106', 106'' and 106''' are depicted in FIGS. 8-10. As shown in the figures, embodiments of the adapter 106 can, for example, include four connector elements 154A-D and an inactive set screw block 156 (as depicted in FIG. 8), three connector elements 154A-C and an active set screw block 156 (as depicted in FIG. 9), or four connector elements 54A-D (as depicted in FIG. 10). Other connector elements/set screw block configurations are also contemplated. As depicted in FIG. 9, where the set screw block is active, the adapter 106 can include a fluid resistant barrier 160.

Figure 11A:
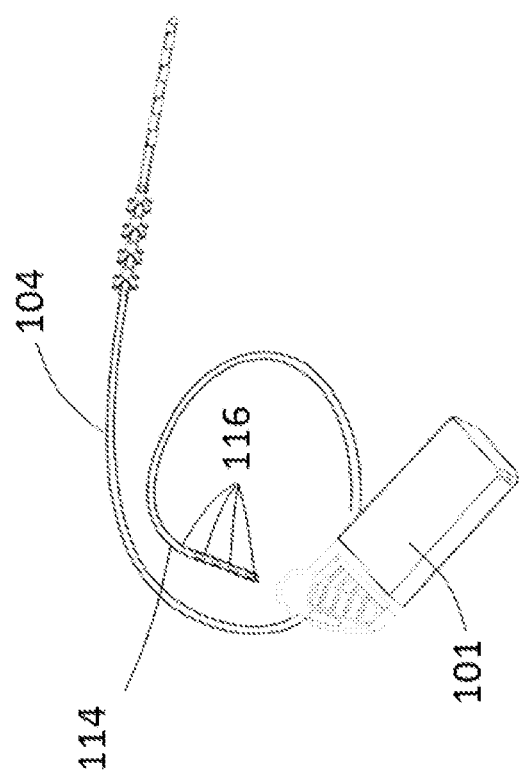
FIG. 11A is an assembly view depicting a previously implanted neurostimulator device and stimulation lead, in accordance with the prior art.
Figure 11B:
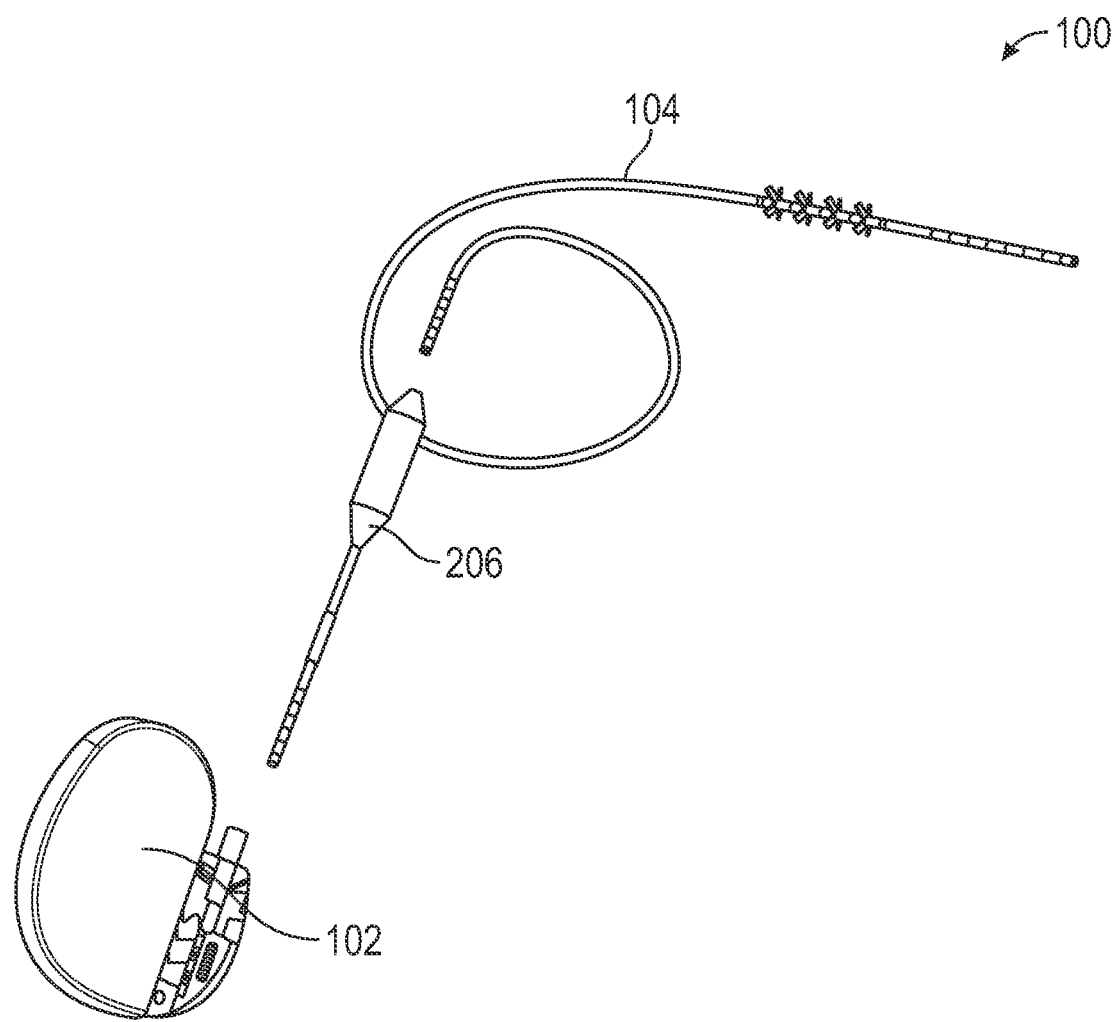
FIG. 11B is an assembly view depicting an adapted neuromodulation system, including a replacement neurostimulator device, previously implanted stimulation lead, and adaptor electrically coupling the otherwise incompatible stimulation lead and replacement neurostimulator device, in accordance with a second embodiment of the disclosure.

FIG. 11A depicts a previously implanted neurostimulator device 101 and stimulation lead 104, wherein the proximal portion 114 of the stimulation lead 104 includes connectors 116 having a pitch spacing about 0.085 inches. FIG. 11B depicts a replacement neurostimulator device 102 configured to mate with a stimulation lead having a pitch spacing of about 0.170 inches. As further depicted in FIG. 11B, an adapter 206 can be used between the stimulation lead 104 and the replacement device 102, thereby providing an electrical coupling between an otherwise incompatible stimulation lead 104 and neurostimulator device 102.

Figure 13:
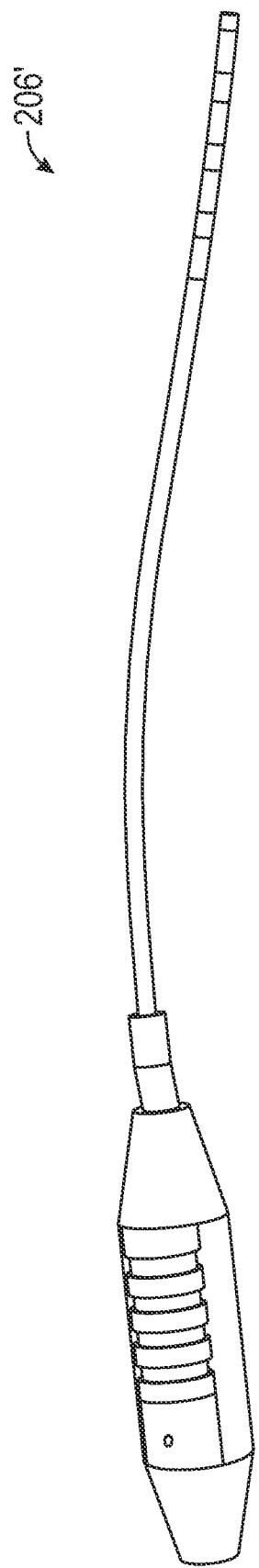
FIG. 13 is a perspective view depicting an adaptor, in accordance with a seventh embodiment of the disclosure.

With additional reference to FIGS. 12A-C, similar to adapter 106, adapter 206 can include a plurality of connector elements 154A-D, set screw block 156, set screw 158, boot 162, and a plurality of electrical conductors 164A-D. As depicted in FIGS. 12B-C, a plan view of the proximal portion 148 and the distal portion 150 are shown depicting example dimensional spacing of the various components, in accordance with one embodiment of the disclosure. FIG. 13 depicts another embodiment of adapter 206', in accordance with the disclosure. Accordingly, in some embodiments, the adapter 206 can be configured to establish a compatible electrical connection of a neurostimulator device 102 generally configured to mate with a stimulation lead 104 having a plurality of electrical connectors 116 spaced apart from one another at a pitch of approximately 0.170 inches (which may be a replacement for a previously implanted neurostimulator device 101), with an implantable stimulation lead 104 having a plurality of electrical connectors 116 spaced apart from one another at a pitch of approximately 0.085 inches (which may have been previously implanted into the patient).

Figures 14A, 14B:
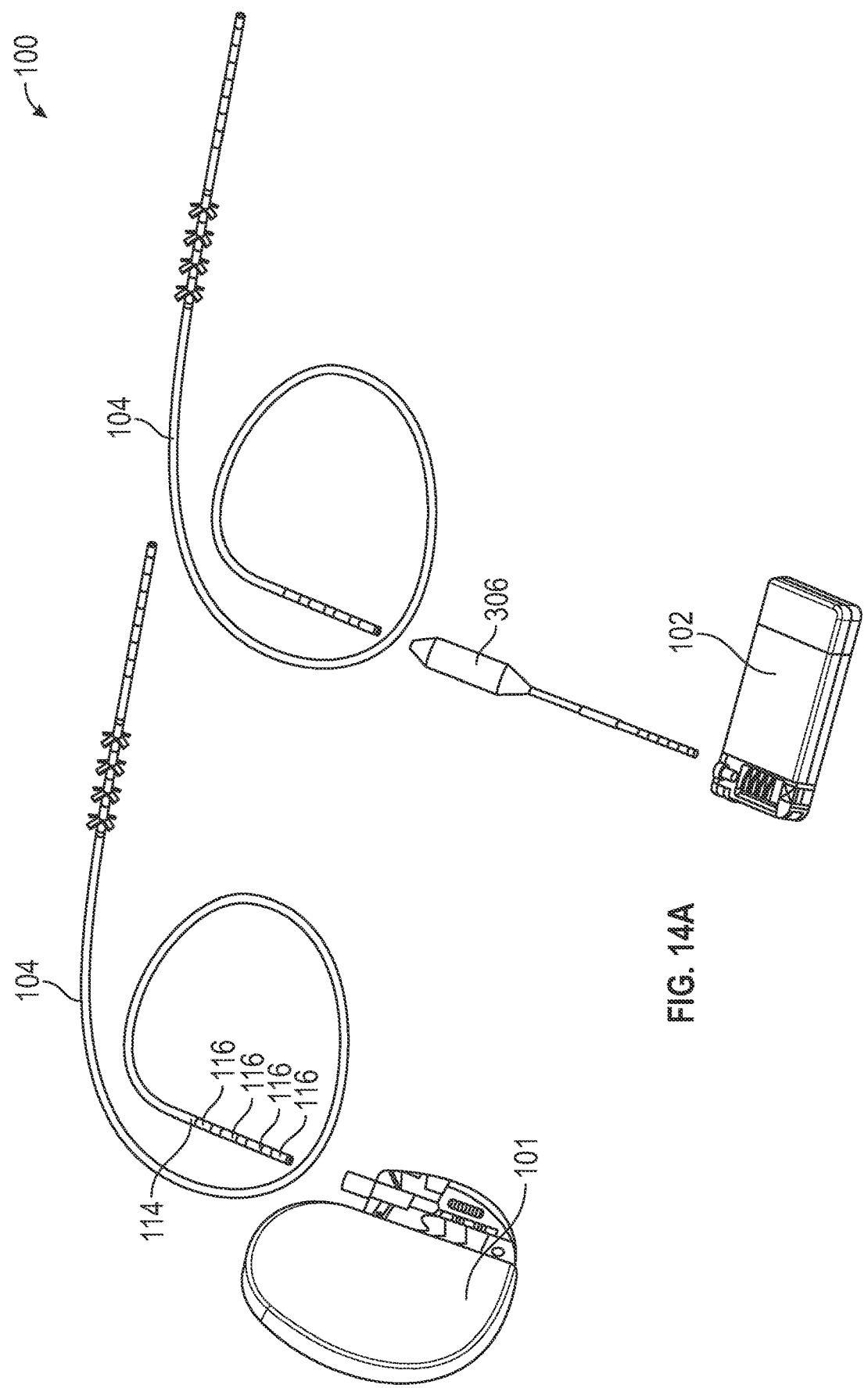
FIG. 14A is an assembly view depicting a previously implanted neurostimulator device and stimulation lead, in accordance with the prior art.
FIG. 14B is an assembly view depicting an adapted neuromodulation system, including a replacement neurostimulator device, previously implanted stimulation lead, and adaptor electrically coupling the otherwise incompatible stimulation lead and replacement neurostimulator device, in accordance with a third embodiment of the disclosure.

FIG. 14A depicts a previously implanted neurostimulator device 101 and stimulation lead 104, wherein the proximal portion 114 of the stimulation lead 104 includes connectors 116 having a pitch spacing about 0.170 inches. FIG. 14B depicts a replacement neurostimulator device 102 configured to mate with a stimulation lead having a pitch spacing of about 2 mm (0.080 inches). As further depicted in FIG. 14B, an adapter 306 can be used between the stimulation lead 104 and the replacement device 102, thereby providing an electrical coupling between an otherwise incompatible stimulation lead 104 and neurostimulator device 102. Accordingly, in some embodiments, the adapter 306 can be configured to establish a compatible electrical connection of a neurostimulator device 102 generally configured to mate with a stimulation lead 104 having a plurality of electrical connectors 116 spaced apart from one another at a pitch of approximately 2 mm (which may be a replacement for a previously implanted neurostimulator device 101), with an implantable stimulation lead 104 having a plurality of electrical connectors 116 spaced apart from one another at a pitch of approximately 0.170 inches (which may have been previously implanted into the patient).

Figure 15A:
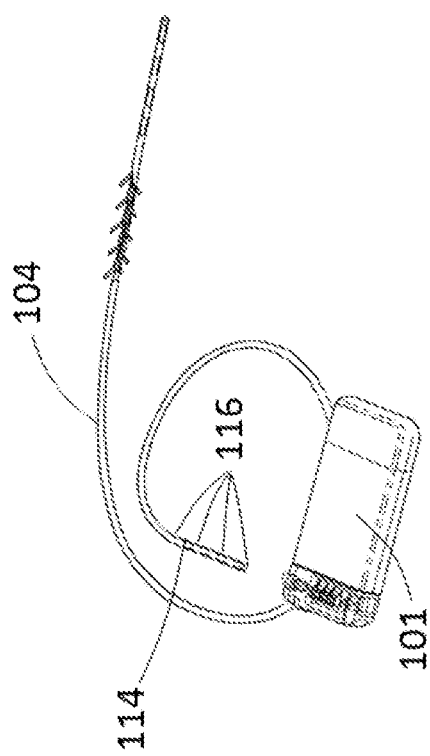
FIG. 15A is an assembly view depicting a previously implanted neurostimulator device and stimulation lead, in accordance with the prior art.
Figure 15B:
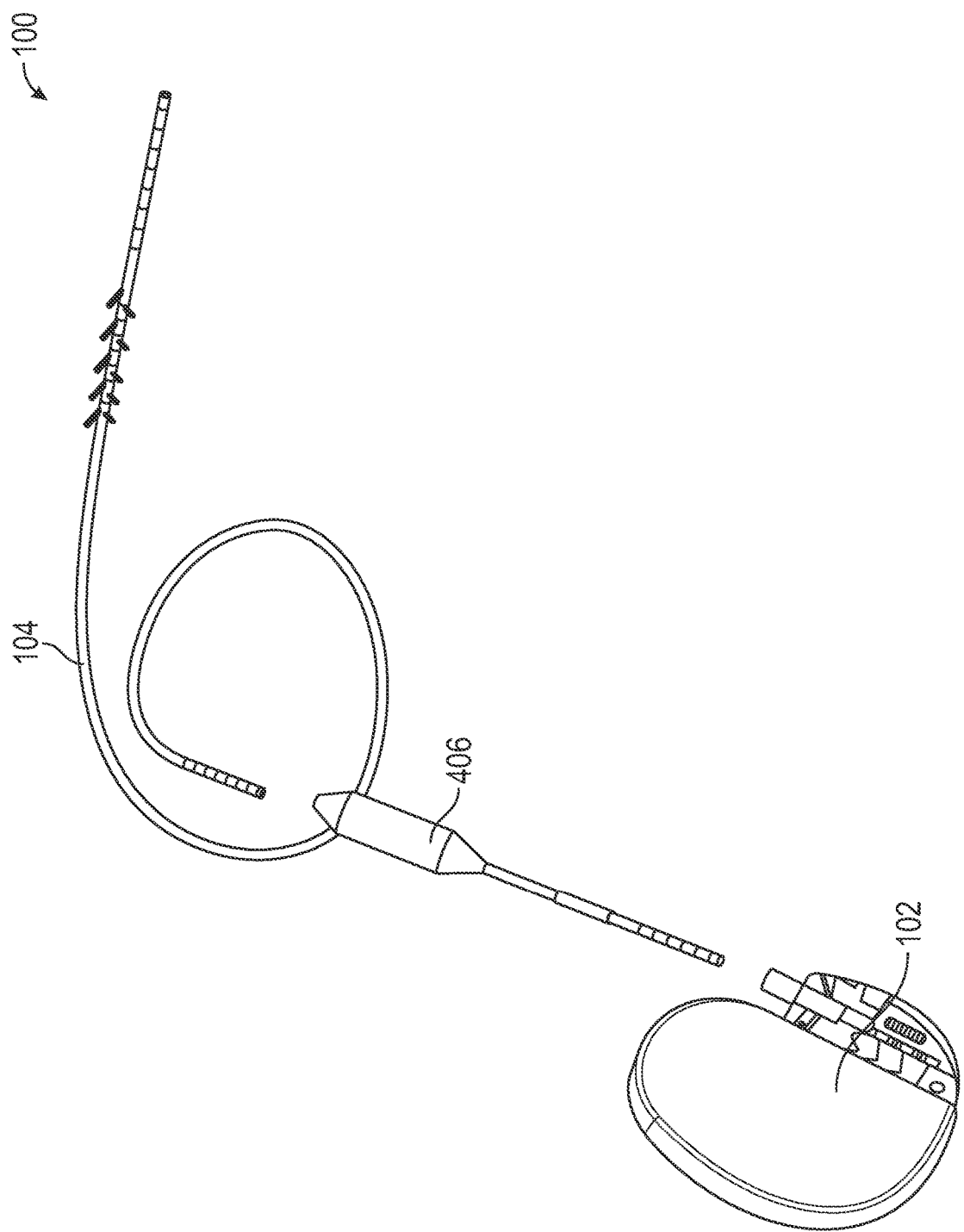
FIG. 15B is an assembly view depicting an adapted neuromodulation system, including a replacement neurostimulator device, previously implanted stimulation lead, and adaptor electrically coupling the otherwise incompatible stimulation lead and replacement neurostimulator device, in accordance with a fourth embodiment of the disclosure.

FIG. 15A depicts a previously implanted neurostimulator device 101 and stimulation lead 104, wherein the proximal portion 114 of the stimulation lead 104 includes connectors 116 having a pitch spacing about 2 mm (0.080 inches). FIG. 15B depicts a replacement neurostimulator device 102 configured to mate with a stimulation lead having a pitch spacing of about 0.170 inches. As further depicted in FIG. 15B, an adapter 406 can be used between the stimulation lead 104 and the replacement device 102, thereby providing an electrical coupling between an otherwise incompatible stimulation lead 104 and neurostimulator device 102. Accordingly, in some embodiments, the adapter 406 can be configured to establish a compatible electrical connection of a neurostimulator device 102 generally configured to mate with a stimulation lead 104 having a plurality of electrical connectors 116 spaced apart from one another at a pitch of approximately 0.170 inches (which may be a replacement for a previously implanted neurostimulator device 101), with an implantable stimulation lead 104 having a plurality of electrical connectors 116 spaced apart from one another at a pitch of approximately 2 mm (which may have been previously implanted into the patient).

Figure 16B:
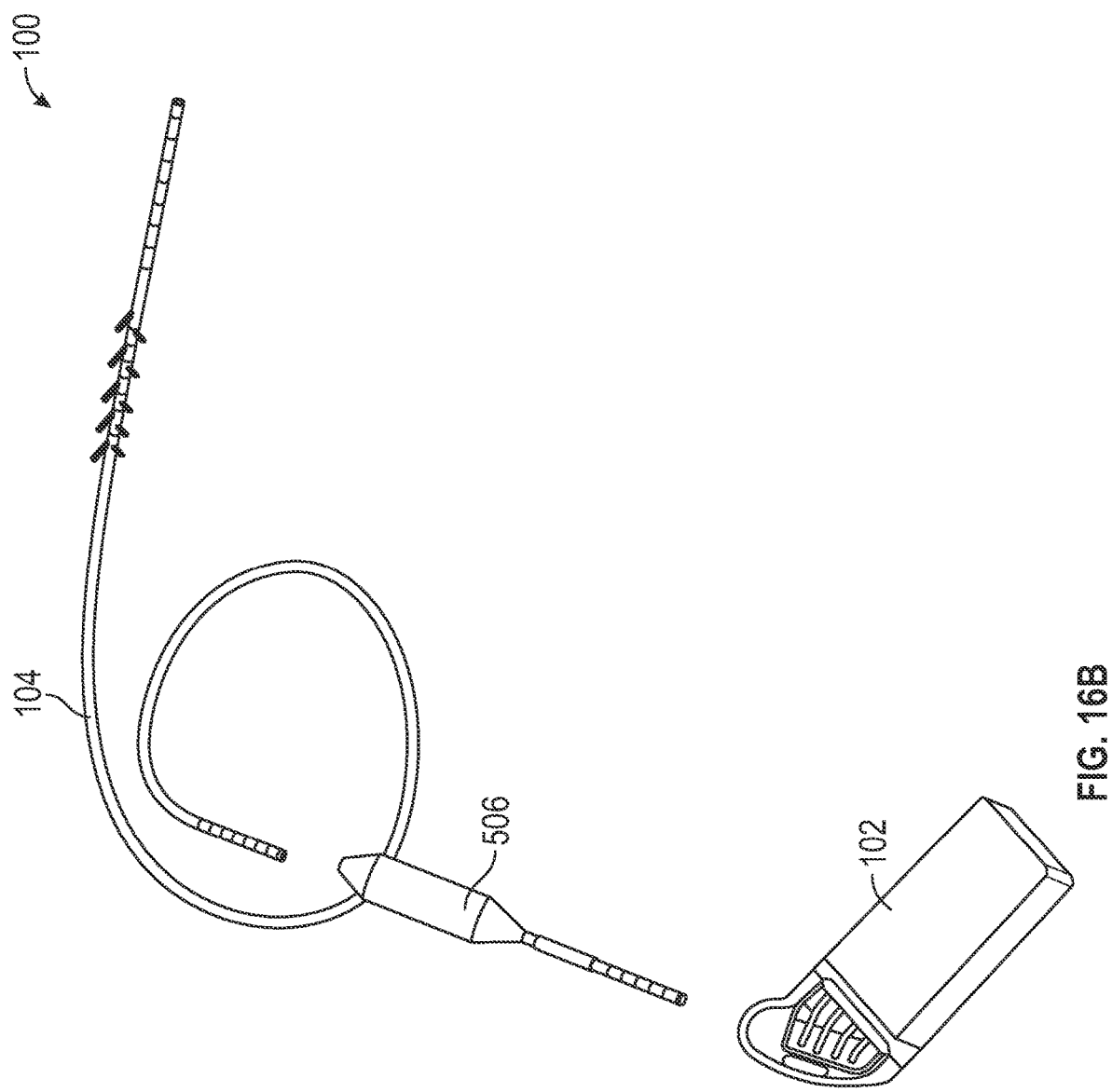
FIG. 16B is an assembly view depicting an adapted neuromodulation system, including a replacement neurostimulator device, previously implanted stimulation lead, and adaptor electrically coupling the otherwise incompatible stimulation lead and replacement neurostimulator device, in accordance with a fifth embodiment of the disclosure.

FIG. 16A depicts a previously implanted neurostimulator device 101 and stimulation lead 104, wherein the proximal portion 114 of the stimulation lead 104 includes connectors 116 having a pitch spacing about 2 mm (0.080 inches). FIG. 16B depicts a replacement neurostimulator device 102 configured to mate with a stimulation lead having a pitch spacing of about 0.085 inches. As further depicted in FIG. 16B, an adapter 506 can be used between the stimulation lead 104 and the replacement device 102, thereby providing an electrical coupling between an otherwise incompatible stimulation lead 104 and neurostimulator device 102. Accordingly, in some embodiments, the adapter 506 can be configured to establish a compatible electrical connection of a neurostimulator device 102 generally configured to mate with a stimulation lead 104 having a plurality of electrical connectors 116 spaced apart from one another at a pitch of approximately 0.085 inches (which may be a replacement for a previously implanted neurostimulator device 101), with an implantable stimulation lead 104 having a plurality of electrical connectors 116 spaced apart from one another at a pitch of approximately 2 mm (which may have been previously implanted into the patient).

Figure 17A:
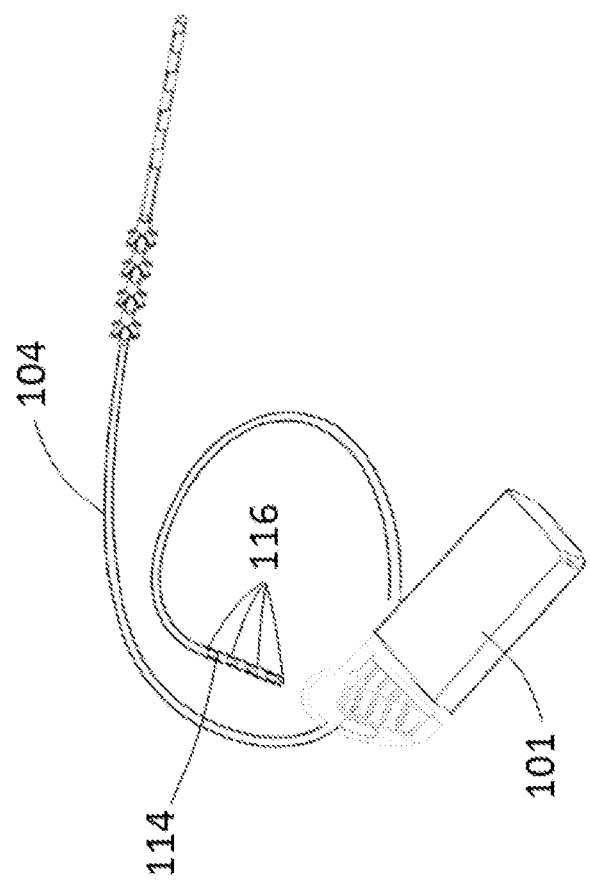
FIG. 17A is an assembly view depicting a previously implanted neurostimulator device and stimulation lead, in accordance with the prior art.
Figure 17B:
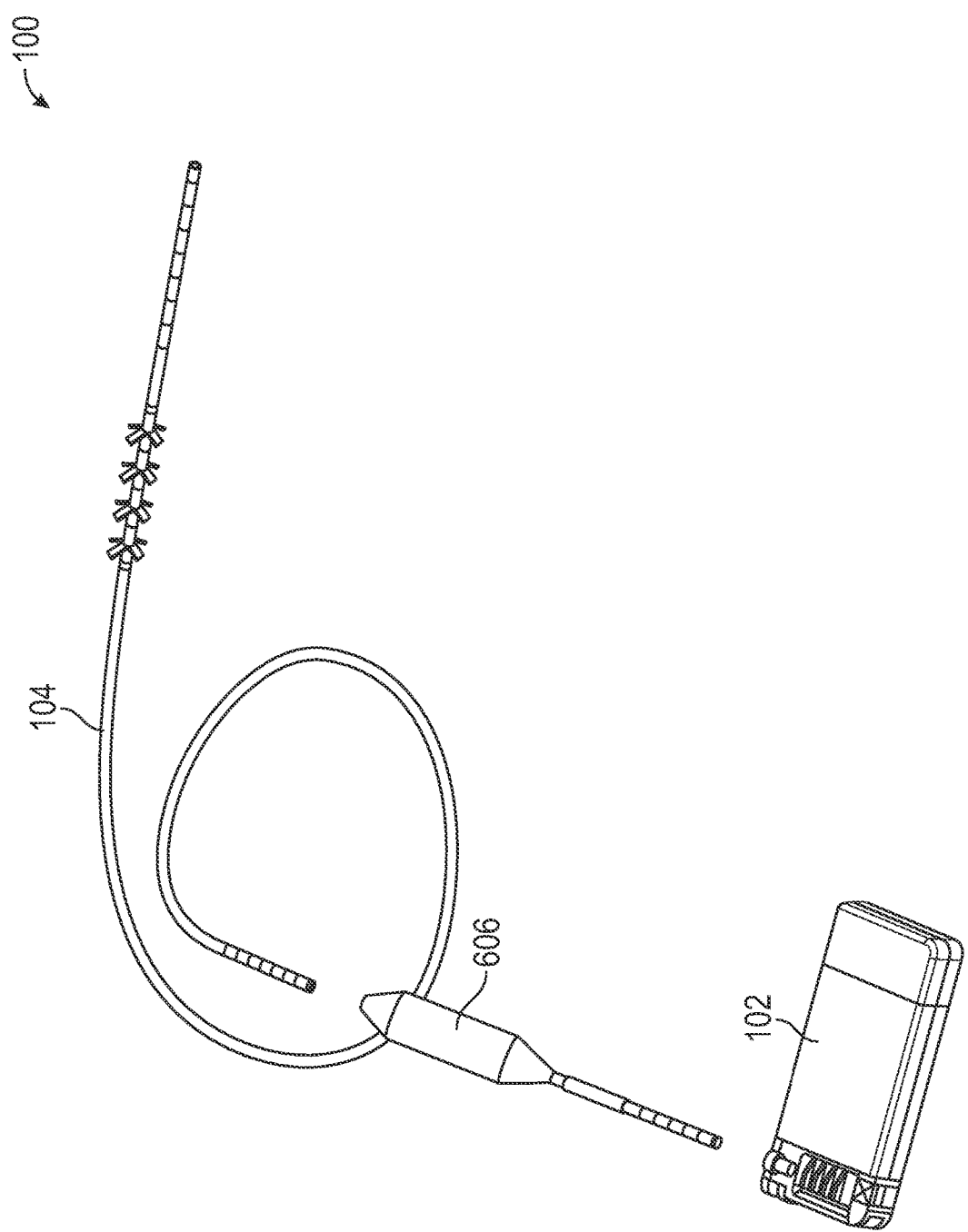
FIG. 17B is an assembly view depicting an adapted neuromodulation system, including a replacement neurostimulator device, previously implanted stimulation lead, and adaptor electrically coupling the otherwise incompatible stimulation lead and replacement neurostimulator device, in accordance with a sixth embodiment of the disclosure.

FIG. 17A depicts a previously implanted neurostimulator device 101 and stimulation lead 104, wherein the proximal portion 114 of the stimulation lead 104 includes connectors 116 having a pitch spacing about 0.085 inches. FIG. 17B depicts a replacement neurostimulator device 102 configured to mate with a stimulation lead having a pitch spacing of about 2 mm (0.080 inches). As further depicted in FIG. 17B, an adapter 606 can be used between the stimulation lead 104 and the replacement device 102, thereby providing an electrical coupling between an otherwise incompatible stimulation lead 104 and neurostimulator device 102. Accordingly, in some embodiments, the adapter 606 can be configured to establish a compatible electrical connection of a neurostimulator device 102 generally configured to mate with a stimulation lead 104 having a plurality of electrical connectors 116 spaced apart from one another at a pitch of approximately 2 mm (which may be a replacement for a previously implanted neurostimulator device 101), with an implantable stimulation lead 104 having a plurality of electrical connectors 116 spaced apart from one another at a pitch of approximately 0.085 inches (which may have been previously implanted into the patient).

Further Examples

16. A neuromodulation adaptor configured to provide an electrical coupling between an otherwise incompatible stimulation lead and neurostimulator device, the neuromodulation adaptor comprising:
 a proximal portion including a plurality of electrical conductors spaced apart at a pitch spacing of approximately 0.170 inches and configured to electrically engage with a corresponding plurality of electrical terminals of a neurostimulator device; and
 a distal portion including plurality of conductor elements and a set screw, the plurality of conductor elements spaced apart at a pitch spacing of approximately 2 millimeters and configured to electrically engage with a corresponding plurality of electrical connectors of a stimulation lead.

17. The neuromodulation adaptor of example 16, wherein the proximal portion includes a forward stop configured to serve as a reference point for spacing of the plurality of electrical conductors relative to a corresponding plurality of electrical terminals of a neurostimulator device.

18. The neuromodulation adaptor of example 16, wherein the distal portion includes an abutting surface configured to serve as a reference point for spacing of the plurality of conductor elements relative to a corresponding plurality of electrical connectors of a stimulation lead.

19. The neuromodulation adaptor of example 16, further comprising a flexible portion located between the proximal portion and the distal portion, configured to enable bending of the neuromodulation adaptor to aid in an ideal positioning of a neurostimulator device relative to a stimulation lead within a body of a patient.

20. A neuromodulation adaptor configured to provide an electrical coupling between an otherwise incompatible stimulation lead and neurostimulator device, the neuromodulation adaptor comprising:
 a proximal portion including a plurality of electrical conductors spaced apart at a pitch spacing of approximately 0.085 inches and configured to electrically engage with a corresponding plurality of electrical terminals of a neurostimulator device; and
 a distal portion including plurality of conductor elements and a set screw, the plurality of conductor elements spaced apart at a pitch spacing of approximately 2 millimeters and configured to electrically engage with a corresponding plurality of electrical connectors of a stimulation lead.

21. The neuromodulation adaptor of example 20, wherein the proximal portion includes a forward stop configured to serve as a reference point for spacing of the plurality of electrical conductors relative to a corresponding plurality of electrical terminals of a neurostimulator device.

22. The neuromodulation adaptor of example 20, wherein the distal portion includes an abutting surface configured to serve as a reference point for spacing of the plurality of conductor elements relative to a corresponding plurality of electrical connectors of a stimulation lead.

23. The neuromodulation adaptor of example 20, further comprising a flexible portion located between the proximal portion and the distal portion, configured to enable bending of the neuromodulation adaptor to aid in an ideal positioning of a neurostimulator device relative to a stimulation lead within a body of a patient.

24. A neuromodulation adaptor configured to provide an electrical coupling between an otherwise incompatible stimulation lead and neurostimulator device, the neuromodulation adaptor comprising:

a proximal portion including a plurality of electrical conductors spaced apart at a pitch spacing of approximately 2 millimeters and configured to electrically engage with a corresponding plurality of electrical terminals of a neurostimulator device; and a distal portion including plurality of conductor elements and an electrically active set screw, the plurality of conductor elements and a set screw spaced apart at a pitch spacing of approximately 0.085 inches and configured to electrically engage with a corresponding plurality of electrical connectors of a stimulation lead.

25. The neuromodulation adaptor of example 24, wherein the proximal portion includes a forward stop configured to serve as a reference point for spacing of the plurality of electrical conductors relative to a corresponding plurality of electrical terminals of a neurostimulator device.

26. The neuromodulation adaptor of example 24, wherein the distal portion includes a datum reference configured to serve as a reference point for spacing of the plurality of conductor elements relative to a corresponding plurality of electrical connectors of a stimulation lead.

27. The neuromodulation adaptor of example 24, further comprising a flexible portion located between the proximal portion and the distal portion, configured to enable bending of the neuromodulation adaptor to aid in an ideal positioning of a neurostimulator device relative to a stimulation lead within a body of a patient.

28. The neuromodulation adaptor of example 24, further comprising a septum configured to provide a fluid resistant seal to inhibit contact between the set screw and a bodily fluid.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A neuromodulation adaptor configured to provide an electrical coupling between an otherwise incompatible stimulation lead and neurostimulator device, the neuromodulation adaptor comprising:

a proximal portion including a plurality of electrical conductors spaced apart at a pitch spacing of approximately 0.085 inches and configured to electrically engage with a corresponding plurality of electrical terminals of a neurostimulator device; and a distal portion including plurality of conductor elements and an electrically active set screw, the plurality of conductor elements and electrically active set screw spaced apart at a pitch spacing of approximately 0.170 inches and configured to electrically engage with a corresponding plurality of electrical connectors of a stimulation lead.

2. The neuromodulation adaptor of claim 1, wherein the proximal portion includes a forward stop configured to serve as a reference point for spacing of the plurality of electrical conductors relative to a corresponding plurality of electrical terminals of a neurostimulator device.

3. The neuromodulation adaptor of claim 1, wherein the distal portion includes a datum reference configured to serve as a reference point for spacing of the plurality of conductor elements relative to a corresponding plurality of electrical connectors of a stimulation lead.

4. The neuromodulation adaptor of claim 1, further comprising a flexible portion located between the proximal portion and the distal portion, configured to enable bending of the neuromodulation adaptor to aid in an ideal positioning of a neurostimulator device relative to a stimulation lead within a body of a patient.

5. The neuromodulation adaptor of claim 1, further comprising a septum configured to provide a fluid resistant seal to inhibit contact between the electrically active set screw and a bodily fluid.

6. A neuromodulation adaptor configured to provide an electrical coupling between an otherwise incompatible stimulation lead and neurostimulator device, the neuromodulation adaptor comprising:

a proximal portion including a plurality of electrical conductors spaced apart at a pitch spacing of approximately 0.170 inches and configured to electrically engage with a corresponding plurality of electrical terminals of a neurostimulator device; and a distal portion including plurality of conductor elements and a set screw, the plurality of conductor elements and a set screw spaced apart at a pitch spacing of approximately 0.085 inches and configured to electrically engage with a corresponding plurality of electrical connectors of a stimulation lead.

7. The neuromodulation adaptor of claim 6, wherein the proximal portion includes a forward stop configured to serve as a reference point for spacing of the plurality of electrical conductors relative to a corresponding plurality of electrical terminals of a neurostimulator device.

8. The neuromodulation adaptor of claim 6, wherein the distal portion includes a datum reference configured to serve as a reference point for spacing of the plurality of conductor elements relative to a corresponding plurality of electrical connectors of a stimulation lead.

9. The neuromodulation adaptor of claim 6, further comprising a flexible portion located between the proximal portion and the distal portion, configured to enable bending of the neuromodulation adaptor to aid in an ideal positioning of a neurostimulator device relative to a stimulation lead within a body of a patient.

10. The neuromodulation adaptor of claim 6, further comprising a septum configured to provide a fluid resistant seal to inhibit contact between the set screw and a bodily fluid.

11. A neuromodulation adaptor configured to provide an electrical coupling between an otherwise incompatible stimulation lead and neurostimulator device, the neuromodulation adaptor comprising:
- a proximal portion including a plurality of electrical conductors spaced apart at a pitch spacing of approximately 2 millimeters and configured to electrically engage with a corresponding plurality of electrical terminals of a neurostimulator device; and
- a distal portion including plurality of conductor elements and an electrically active set screw, the plurality of conductor elements and a set screw spaced apart at a pitch spacing of approximately 0.170 inches and configured to electrically engage with a corresponding plurality of electrical connectors of a stimulation lead.

12. The neuromodulation adaptor of claim 11, wherein the proximal portion includes a forward stop configured to serve as a reference point for spacing of the plurality of electrical conductors relative to a corresponding plurality of electrical terminals of a neurostimulator device.

13. The neuromodulation adaptor of claim 11, wherein the distal portion includes a datum reference configured to serve as a reference point for spacing of the plurality of conductor elements relative to a corresponding plurality of electrical connectors of a stimulation lead.

14. The neuromodulation adaptor of claim 11, further comprising a flexible portion located between the proximal portion and the distal portion, configured to enable bending of the neuromodulation adaptor to aid in an ideal positioning of a neurostimulator device relative to a stimulation lead within a body of a patient.

15. The neuromodulation adaptor of claim 11, further comprising a septum configured to provide a fluid resistant seal to inhibit contact between the electrically active set screw and a bodily fluid.

* * * * *